United States Patent [19]
Hoehn

[11] 3,935,222
[45] Jan. 27, 1976

[54] 1,4,5,7-TETRAHYDROPYRAZOLO[3,4-B]PYRIDIN-6-ONES

[75] Inventor: Hans Hoehn, Tegernheim, Germany

[73] Assignee: E. R. Squibb & Sons, Inc., Princeton, N.J.

[22] Filed: Apr. 16, 1975

[21] Appl. No.: 568,754

[52] U.S. Cl.............. 260/295.5 B; 260/294.8 R; 260/296 H; 260/310 R; 424/263; 424/266
[51] Int. Cl.² ........................................ C07D 471/06
[58] Field of Search ... 260/295.5 B, 296 H, 294.8 R

[56] References Cited
OTHER PUBLICATIONS
Checchi et al., *Gazz. Chim. Ital.*, Vol. 85, (1955), pp. 1160–1170.

*Primary Examiner*—Henry R. Jiles
*Assistant Examiner*—Robert W. Ramsuer
*Attorney, Agent, or Firm*—Lawrence S. Levinson; Merle J. Smith

[57] ABSTRACT

The new derivatives of tetrahydropyrazolo[3,4-b]-pyridin-6-ones and their acid addition salts which have the general formula:

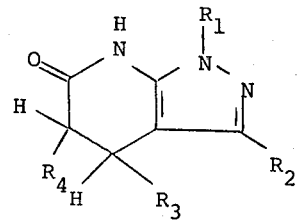

and salts thereof are useful as central nervous system depressants and anti-inflammatory agents.

16 Claims, No Drawings

1,4,5,7-TETRAHYDROPYRAZOLO[3,4-B]PYRIDIN-6-ONES

SUMMARY OF THE INVENTION

The invention relates to new 1,4,5,7-tetrahydropyrazolo [3,4-b]pyridin-6-ones and salts thereof having the general formula (I)

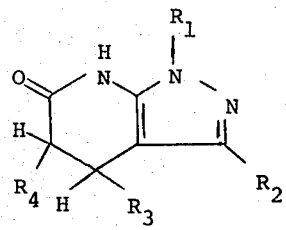

The symbols have the following meanings in formula I and throughout this specification:

$R_1$ represents hydrogen, lower alkyl, phenyl, phenyl-lower alkyl or furfuryl.

$R_2$ represents hydrogen, lower alkyl or phenyl.

$R_3$ represents hydrogen, lower alkyl, tri(halo)lower alkyl or phenyl.

$R_4$ represents hydrogen, carboxy or carbo-lower alkoxy.

The lower alkyl groups in any of the foregoing radicals include straight or branched chain hydrocarbon groups containing 1 to 7 carbon atoms. Examples of the groups contemplated are methyl, ethyl, propyl, isopropyl, etc. Lower alkyl groups of 1 to 4 carbon atoms are preferred, especially the 1, 2 and 3 carbon members of this group. The phenyl-lower alkyl and lower alkoxy groups contain lower alkyl group of such description. The four common halogens are contemplated with fluorine preferred.

Preferred embodiments of this invention are as follows:

$R_1$ is hydrogen or lower alkyl of 1 to 4 carbon atoms, especially methyl and ethyl.

$R_2$ is hydrogen or lower alkyl, especially hydrogen and methyl.

$R_3$ is hydrogen, lower alkyl, tri(halo)lower alkyl or phenyl, especially methyl, trifluoromethyl, ethyl, propyl and phenyl.

$R_4$ is hydrogen, carboxy and carboethoxy.

DETAILED DESCRIPTION

The new compounds of formula I can be produced by several methods. The symbols in the structural formulas have the same meaning as previously described.

According to one procedure a product of formula I is obtained by reacting a 5-aminopyrazole of the formula (II)

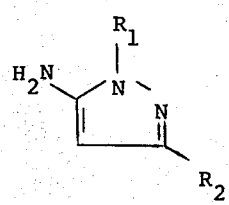

[prepared according to the procedure described in Z.f. Chemie 10, 386–388 (1970)] with an alkylidene or arylidene malonic ester of the formula (III)

wherein R is lower alkyl or aryl, in the presence of a solvent, e.g., dimethylformamide at reflux temperature. The addition of an equivalent amount of water causes decarboxylation.

Since the foregoing reaction of 5-aminopyrazole and the unsaturated ethyl malonate proceeds stepwise via the ester of the formula (IV)

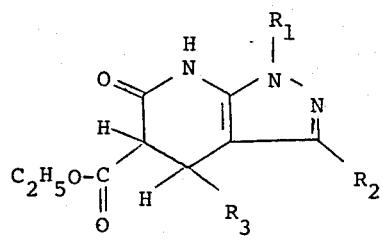

and the acid of the formula (V)

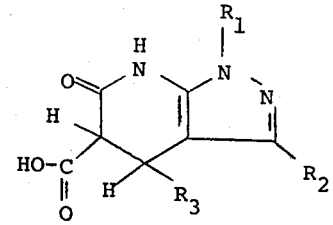

the respective compounds of formulas IV and V can be isolated for the purpose of biological use or for employment as intermediates, e.g., for producing esters with branched alcohols, acid chlorides, amides or for converting into alcohols, etc. For this purpose, the heating time is shortened.

The free acid is obtained from the ester of formula IV by hydrolysis, for example, by treatment with aqueous sodium hydroxide solution. Decarboxylation of the free acid of formula V, e.g., by heating at reflux, provides compounds of formula I in which $R_4$ is hydrogen.

According to another procedure, a product of formula I is produced from a compound of the formula (VI)

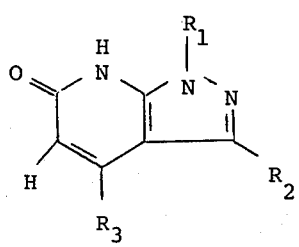

The compounds of formula VI are formed by the following sequence. A 5-aminopyrazole of formula II is made to react with a β-keto ester of the formula (VII) 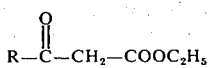

to give the hydroxy ester of the formula (VIII) 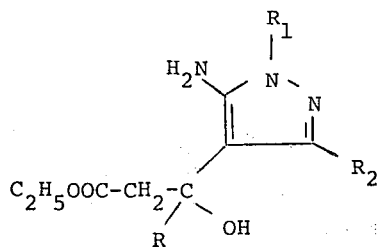

which, in the presence of a solvent like glacial acetic acid at reflux temperature, undergoes ring closure to give a compound of formula VI. The product of formula I is then prepared by catalytic hydrogenation of the compound of formula VI in the presence of a catalyst, e.g., rhodium on charcoal, carried out in an autoclave.

The compounds of formula I form salts which are also part of this invention. The salts include acid-addition salts, particularly the non-toxic, physiologically acceptable members. The basic members of formula I form salts by reaction with a variety of inorganic and organic acids providing acid addition salts including, for example, hydrohalides (especially hydrochloride and hydrobromide), sulfate, nitrate, borate, phosphate, oxalate, tartrate, malate, citrate, acetate, ascorbate, succinate, benzenesulfonate, methanesulfonate, cyclohexanesulfamate and toluenesulfonate. The acid addition salts frequently provide a convenient means for isolating the product, especially in crystalline form, e.g., by forming and precipitating the salt in an appropriate medium in which the salt is insoluble, then after separation of the salt, neutralizing with a base such as barium hydroxide or sodium hydroxide, to obtain the free base of formula I. Other salts can be formed from the free base by reaction with an equivalent of acid.

The new compounds of this invention are central nervous system depressants and may be used as tranquilizers or ataractic agents for the relief of anxiety and tension states, for example, in mice, cats, rats, dogs and other mammalian species, in the same manner as chlordiazepoxide. For this purpose a compound or mixture of compounds of formula I, or non-toxic, physiologically acceptable acid addition salt thereof, is administered orally or parenterally in a conventional dosage form such as tablet, capsule, injectable or the like. A single dose, or preferably 2 to 4 divided daily doses, provided on a basis of about 1 to 50 mg. per kilogram per day, preferably about 2 to 15 mg. per kilogram per day, is appropriate. These compounds are conventionally formulated in a oral or parenteral dosage form by compounding about 10 to 250 mg. per unit of dosage with conventional vehicle, excipient, binder, preservative, stabilizer, flavor or the like as called for by accepted pharmaceutical practice.

The new compounds of this invention also have antiinflammatory properties and are useful as antiinflammatory agents, for example, to reduce local inflammatory conditions such as those of an edematous nature or resulting from proliferation of connective tissue in various mammalian species such as rats, dogs and the like when given orally in dosages of about 5 to 50 mg/kg/day, preferably 5 to 25 mg/kg/day, in single or 2 to 4 divided doses, as indicated by the carageenan edema assay in rats. The active substance can be utilized in compositions such as tablets, capsules, solutions or suspensions containing up to about 300 mg. per unit of dosage of a compound or mixture of compounds of formula I or physiologically acceptable acid addition salt thereof. They are compounded in conventional manner as described above. Topical preparations containing about 0.01 to 3 percent by weight of active substance in a lotion or cream can also be used.

The following examples are illustrative and serve as models for additional compounds within the scope of this invention. All temperatures are in degrees celsius.

EXAMPLE 1

1-Ethyl-1,4,5,7-tetrahydro-3,4-dimethyl-6H-pyrazolo[3,4-b]-pyridin-6-one 104 g. of ethylidenemalonic acid diethyl ester (0.56 mol.), 70 g. of 1-ethyl-5-amino-3-methylpyrazole (0.56 mol.), 480 ml. of dimethylformamide and 20.2 ml. of water (1.12 mol.) are heated at reflux temperature for 94 hours. After removing the solvent in vacuo, the oily product begins to crystallize slowly. Recrystallization from a mixture of ethyl acetate and petroleum ether (1:1) yields 57 g. (53%) of 1-ethyl-1,4,5,7-tetrahydro-3,4-dimethyl-6H-pyrazolo[3,4-b]pyridin-6-one, m.p. 141°–142°.

EXAMPLE 2

1-Ethyl-1,4,5,7-tetrahydro-3,4-dimethyl-6H-pyrazolo[3,4-b]-pyridin-6-one, hydrochloride 23.4 G. of 1-ethyl-1,4,5,7-tetrahydro-3,4-dimethyl6H-pyrazolo[3,4-b]pyridin-6-one (0.12 mol.) are dissolved in 70 ml. of absolute ethanol while warming. After cooling, 32 ml. of ethereal hydrochloric acid (0.2 mol.HCl/l) are added to the solution. Two hours later, 100 ml. of absolute ether are added and the mixture is let stand overnight. The crystallized 1-ethyl-1,4,5,7-tetrahydro-3,4-dimethyl-6H-pyrazolo[3,4-b]pyridin-6-one, hydrochloride is filtered off and dried at 50°, yield 25.3 g. (92%), m.p. 192°–195° (dec.).

EXAMPLE 3

1-Ethyl-1,4,5,7-tetrahydro-4-Phenyl-6H-pyrazolo[3,4-b]pyridin-6-one a. 1-Ethyl-1,4,5,7-tetrahydro-6-oxo-4-phenyl-1H-pyrazolo-[3,4-b]pyridin-6-one-5-carboxylic acid and ethyl ester 49.6 G. of benzylidenemalonic acid diethyl ester (0.2 mol.), 22.2 g. of 1-ethyl-5-aminopyrazole (0.2 mol.) and 200 ml. of absolute dimethylformamide are heated together at reflux temperature for 7 days. After 5 days the ethanol formed by the reaction is distilled off until the boiling point of the dimethylformamide is reached. Then the solution is evaporated as much as possible at 90° in vacuo. The residue is treated four times each with 500 ml. of ether giving 28.5 g. (50%) of 1-ethyl-1,4,5,7-tetrahydro-6-oxo-4-phenyl-1H-pyrazolo[3,4-b]pyridine-5-carboxylic acid.

The ethereal extracts are combined and evaporated in vacuo. Filtering off the crystals gives 5.7 g. (9%) of 1-ethyl-1,4,5,7tetrahydro-6-oxo-4-phenyl-1H-pyrazolo[3,4-b]-pyridine-5-carboxylic acid, ethyl ester which is recrystallized from a mixture of hexane/benzene (2:1) and melts at 143°–144°.

b. 1-Ethyl-1,4,5,7-tetrahydro-4-phenyl-6H-pyrazolo[3,4-b]-pyridin-6-one, hydrochloride 6 g. of 1-ethyl-1,4,5,7-tetrahydro-6-oxo-4-phenyl-1H-pyrazolo[3,4-b]pyridine-5-carboxylic acid (0.0167 mol.) and 30 ml. of dimethylformamide are heated at reflux for 33 hours. Then the solvent is removed in vacuo and the residue dissolved in benzene. After removing a little amorphous product, ethereal hydrochloric acid and a few drops of alcohol are added to the clear benzene solution. The precipitated 1-ethyl-1,4,5,7-tetrahydro-4-phenyl-6H-pyrazolo[3,4-b]pyridin-6-one, hydrochloride is recrystallized from ethanol, yield 3.32 g. (56%), m.p. 246°–247° (dec.).

EXAMPLE 4

1-Ethyl-1,4,5,7-tetrahydro-4-propyl-6H-pyrazolo[3,4-b]pyridine-6-one a. 1-Ethyl-1,4,5,7-tetrahydro-6-oxo-4-propyl-1H-pyrazolo[3,4-b]-pyridine-5-carboxylic acid, ethyl ester, hydrochloride A mixture of 172 g. of butylidenemalonic acid diethyl ester (0.8 mol.), 89 g. of 1-ethyl-5-aminopyrazole (0.8 mol.), 670 ml. of dimethylformamide and 28.8 ml. of water (1.6 mol.) are heated at reflux temperature for 90 hours, after which the dimethylformamide and water are distilled off in vacuo. The oily crude product is then dissolved in 500 ml. of benzol, 100 ml. of alcoholic hydrochloric acid (330 g/l) are added and the mixture is left overnight in the refrigerator. The precipitated hydrochloride is filtered off, washed with 90 ml. of benzol/absolute alcohol (2:1) and dried at 70° to give 95.6 g. (38%) of 1-ethyl-1,4,5,7-tetrahydro-6-oxo-4-propyl-1H-pyrazolo[3,4,-b]pyridine-5-carboxylic acid, ethyl ester, hydrochloride, m.p. 175°–176° (dec.). Recrystallization from acetonitrile yields the pure product, m.p. 180°–181° (dec.).

b. 1-Ethyl-1,4,5,7-tetrahydro-6-oxo-4-propyl-1H-pyrazolo [3,4-b]pyridine-5-carboxylic acid 13.6 G. of 1-ethyl-1,4,5,7-tetrahydro-6-oxo-4-propyl-1H-pyrazolo[3,4-b]pyridine-5-carboxylic acid, ethyl ester, hydrochloride in 160 ml. of 2.5N aqueous sodium hydroxide are stirred at room temperature for 3 hours. The clear solution is allowed to stand overnight. The solution is then acidified with concentrated hydrochloric acid and the crude precipitate, after decanting off the water, is treated with acetonitrile and filtered off. Drying at 60° yields 9 g. (83%) of 1-ethyl-1,4,5,7-tetrahydro-6-oxo-4-propyl-1H-pyrazolo[3,4-b pyridine-5-carboxylic acid, m.p. 126°–127°. Recrystallization from methanol (90%) raises the melting point to 128°–129° (dec.).

c. 1-Ethyl-1,4,5,7-tetrahydro-4-propyl-6H-pyrazolo[3,4-b]-pyridin-6-one

20 G. of 1-ethyl-1,4,5,7-tetrahydro-6-oxo-4-propyl-1H-pyrazolo[3,4-b]pyridine-5-carboxylic acid (0.08 mol.) in 80 ml. of dimethylformamide are heated at reflux temperature for 20 hours. After this time, the dimethylformamide is removed in vacuo and the residual 1-ethyl-1,4,5,7-tetrahydro-4-propyl-6H-pyrazolo[3,4,-b]pyridin-6-one is recrystallized from a mixture of petroleum ether and ethyl acetate (1:1), yield 10.7 g.; (65%), m.p. 108°–110°.

EXAMPLE 5

1-Ethyl-1,4,5,7-tetrahydro-4-methyl-6H-pyrazolo[3,4,-b]pyridin-6-one hydrochloride By replacing benzylidenemalonic acid diethyl ester with ethylenemalonic acid diethyl ester in Example 3, 1-ethyl-1,4,5,7-tetrahydro-4-methyl-6H-pyrazolo[3,4,-b]pyridin-6-one is formed which, in turn, is converted to its hydrochloride by the procedure of Example 2, m.p. 236°–237° (abs. ethanol).

EXAMPLE 6

1-Ethyl-1,4,5,7-tetrahydro-4-ethyl-6H-pyrazolo[3,4-b]pyridin-6-one, hydrochloride By replacing ethylidenemalonic acid, diethyl ester with propylidenemalonic acid diethyl ester in Example 1, 1-ethyl-1,4,5,7-tetrahydro-4-ethyl-6H-pyrazolo[3,4-b]pyridin-6-one is formed which, in turn, is converted to its hydrochloride according to the procedure of Example 2, m.p. 203°–204° (acetonitrile).

The following additional products are made by the procedure of Example 1.

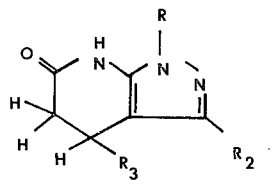

| Example | $R_1$ | $R_2$ | $R_3$ | m.p. |
|---|---|---|---|---|
| 7 | $C_2H_5$ | $CH_3$ | $CH_3-CH_2-CH_2-$ | 113–115° (ethyl acetate/petroleum ether) |
| 8 | $C_2H_5$ | $CH_3$ | $CH_3-CH_2-$ | 141–142° (ethyl acetate/petroleum ether) |
| 9 | $CH_3$ | $CH_3$ | $CH_3-CH_2-CH_2-$ | 150–152° (ethyl acetate/petroleum ether) |
| 10 | ⟨furfuryl⟩-$CH_2-$ | $CH_3$ | $CH_3$ | 136–138° (ethyl acetate) |
| 11 | $CH_3$ | $CH_3$ | $CH_3$ | 189–191° (ethyl acetate) |
| 12 | H | $CH_3-CH_2-CH_2-$ | $CH_3-CH_2-$ | |
| 13 | ⟨phenyl⟩ | $CH_3$ | $CH_3$ | ($R_4 = COOCH_3$) |

-continued

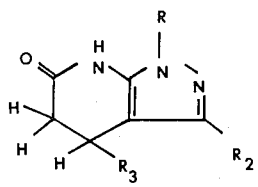

| Example | $R_1$ | $R_2$ | $R_3$ | m.p. |
|---|---|---|---|---|
| 14 | $CH_3$ | $CH_3-CH_2-CH_2-$ | phenyl | |
| 15 | H | $CH_3$ | $CH_3-CH_2-CH_2-CH_2-$ | |
| 16 | phenyl-$CH_2-$ | H | $CH_3$ | |
| 17 | phenyl | H | H | |
| 18 | $C_2H_5$ | H | phenyl | |
| 19 | $C_2H_5$ | phenyl | $CH_3$ | |

EXAMPLE 20

1-Ethyl-1,4,5,7-tetrahydro-4-(trifluoromethyl)-6H-pyrazolo-[3,4-b]pyridine-6-one a. 5-Amino-1-ethylpyrazole-4-(3-hydroxy-3-trifluoromethyl) propionic acid, ethyl ester 3.3 G. of 1-ethyl-5-aminopyrazole (0.03 mol.) and 5.4 g. of α, α, αtrifluoroacetoacetic acid ethyl ester (0.03 mol.) are dissolved in 30 ml. of benzene at room temperature with stirring. The solution is let stand for about 20 hours, during which time 5-amino-1-ethylpyrazole-4-(3-hydroxy-3-trifluoromethyl)propionic acid, ethyl ester crystallizes, 8.2 g. (92.5%), m.p. 135°–137°.

b. 1-Ethyl-1,7-dihydro-4-(trifluoromethyl)-6H-pyrazolo[3,4-b]-pyridin-6-one 5.9 G. of 5-amino-1-ethylpyrazole-4-(3-hydroxy-3-trifluoromethyl)propionic acid, ethyl ester (0.02 mol.) in 60 ml. of glacial acetic acid are heated at reflux for five hours. After cooling, the clear solution is evaporated in vacuo and the residue treated with water. The 1-ethyl-1,7-dihydro-4-(trifluoromethyl)-6H-pyrazolo[3,4-b]pyridine-6-one is filtered off and dried in a dessicator over phosphorus pentoxide, yield 4.48 g. (97%); m.p. 178°–179°. A sample recrystallized from cyclohexane melts at 179°–180°.

c. 1-Ethyl-1,4,5,7-tetrahydro-4-(trifluoromethyl)-6H-pyrazolo[3,4-b]pyridin-6-one 16.2 G. of 1-ethyl-1,7-dihydro-4-(trifluoromethyl)-6H-pyrazolo[3,4-b]pyridin-6-one, dissolved in 250 ml. of absolute ethanol, are catalytically hydrogenated by means of rhodium on charcoal catalyst (5%) at a temperature of 90°–100°. The reaction is performed in an autoclave at a hydrogen pressure of 10 atm. for 14 hours. After cooling, the catalyst is filtered off and the solution evaporated to dryness. The residual 1-ethyl-1,4,5,7-tetrahydro-4-(trifluoromethyl)-6H-pyrazolo[3,4-b]pyridin-6-one is treated with hot hexane providing 13.3 g. (81.5%) of the compound, m.p. 129°–130°. Recrystallization from a mixture of benzene/petroleum ether (1:2) raises the melting point at 130°–132°.

What is claimed is:

1. A compound of the formula

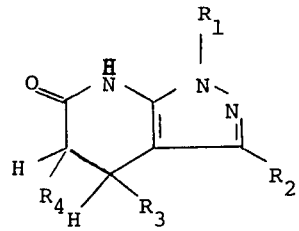

wherein $R_1$ is hydrogen, lower alkyl, phenyl, phenyl-lower alkyl or furfuryl; $R_2$ is hydrogen, lower alkyl or phenyl; $R_3$ is hydrogen, lower alkyl, tri(halo)lower alkyl or phenyl, and $R_4$ is hydrogen, carboxy or carbo-lower alkoxy, and acid addition salts thereof.

2. A compound as in claim 1 wherein $R_1$ is hydrogen or $C_1$ to $C_4$ alkyl; $R_2$ is hydrogen or lower alkyl; $R_3$ is hydrogen, lower alkyl, tri(halo)lower alkyl or phenyl; and $R_4$ is hydrogen, carboxy or carboethoxy.

3. A compound as in claim 1 wherein $R_1$ is hydrogen, methyl or ethyl; $R_2$ is hydrogen or methyl; $R_3$ is methyl, trifluoromethyl, ethyl, propyl or phenyl; and $R_4$ is hydrogen, carboxy or carboethoxy.

4. A compound as in claim 1 wherein $R_1$ is ethyl and $R_4$ is hydrogen.

5. A compound as in claim 1 wherein $R_1$, $R_2$ and $R_3$ each is lower alkyl and $R_4$ is hydrogen.

6. A compound as in claim 1 wherein $R_1$ and $R_3$ each is lower alkyl, and $R_2$ and $R_4$ each is hydrogen.

7. A compound as in claim 1 wherein $R_1$ is lower alkyl, $R_2$ and $R_4$ each is hydrogen and $R_3$ is tri(halo)-lower alkyl.

8. A compound as in claim 1 wherein $R_1$ is lower alkyl, $R_2$ and $R_4$ each is hydrogen and $R_3$ is phenyl.

9. A compound as in claim 1 wherein $R_1$ and $R_3$ each is lower alkyl, $R_2$ is hydrogen and $R_4$ is carboxy.

10. A compound as in claim 1 wherein $R_1$ is ethyl, $R_2$ and $R_3$ each is methyl and $R_4$ is hydrogen.

11. A compound as in claim 1 wherein $R_1$ is ethyl, $R_2$ and $R_4$ each is hydrogen and $R_3$ is methyl.

12. A compound as in claim 1 wherein $R_1$ is ethyl, $R_2$ and $R_4$ each is hydrogen and $R_3$ is trifluoromethyl.

13. A compound as in claim 1 wherein $R_1$ is ethyl, $R_2$ and $R_4$ each is hydrogen and $R_3$ is phenyl.

14. A compound as in claim 1 wherein $R_1$ and $R_3$ each is ethyl and $R_2$ and $R_4$ each is hydrogen.

15. A compound as in claim 1 wherein $R_1$ is ethyl, $R_2$ is hydrogen, $R_3$ is n-propyl and $R_4$ is carboethoxy.

16. A compound as in claim 1 wherein $R_1$ is ethyl, $R_2$ and $R_3$ each is methyl and $R_4$ is hydrogen.

* * * * *